US007533987B2

(12) United States Patent
Tsai

(10) Patent No.: US 7,533,987 B2
(45) Date of Patent: May 19, 2009

(54) METHOD FOR EXERCISING EYE MUSCLE

(76) Inventor: Hong-Bing Tsai, 2F., No. 4, Lane 47, Chien Kung 1st Rd., Hsinchu City (TW)

( * ) Notice: Subject to any disclaimer, the term of this patent is extended or adjusted under 35 U.S.C. 154(b) by 194 days.

(21) Appl. No.: 11/755,749

(22) Filed: May 31, 2007

(65) Prior Publication Data

US 2008/0300514 A1 Dec. 4, 2008

(51) Int. Cl.
*A61B 3/00* (2006.01)

(52) U.S. Cl. ...................................... 351/203; 351/246

(58) Field of Classification Search ................. 351/200, 351/201, 203, 223, 237, 239, 243, 244, 246
See application file for complete search history.

(56) References Cited

U.S. PATENT DOCUMENTS 5,422,688 A * 6/1995 Asea .......................... 351/203
2005/0007550 A1* 1/2005 Turkov et al. ............... 351/203

* cited by examiner

*Primary Examiner*—William C Choi
*Assistant Examiner*—Jack Dinh
(74) *Attorney, Agent, or Firm*—Leong C. Lei

(57) ABSTRACT

The method provides an exercising environment which contains a display device positioned on a platform, a servo motor to move the platform forward towards a trainee or backward away from the trainee, an illuminating device producing lighting to the exercising environment a switch to turn on and off the illuminating device, and a computing device controlling a video or image displayed on the display device. Then, while the trainee is watching the video or image shown on the display device, by adjusting the distance of the display device to the trainee, the brightness of the illuminating device, and the location of the image on the display device, ail within appropriate ranges and at appropriate frequencies, the ciliary body, the iris, and the extraocular muscles of the trainee's eyes are automatically exercised by the method without boring the trainee.

8 Claims, 2 Drawing Sheets

METHOD FOR EXERCISING EYE MUSCLE

TECHNICAL FIELD OF THE INVENTION

The present invention generally relates to eyesight improvements, and more particularly to a method for exercising eye muscles.

DESCRIPTION OF THE PRIOR ART

The function of human eye mainly involves three sets of muscles: the ciliary body adjusts the thickness of the lens; six extraocular muscles control the movement of the eyeball; arid the iris adjusts the aperture of the pupil. Constantly exercising these sets of muscles to maintain their flexibility is a well known approach to preserve or improve the eyesight.

People can see both distant and nearby objects clearly because the lens of die eye is adjusted to bring the objects focused. When the ciliary body contracts, the lens becomes thicker to see nearby objects clearly; and, when the ciliary body relaxes, the lens becomes thinner to see distant objects clearly. In other words, the ciliary body would automatically contract or relax when a person gazes a nearby or distant object. The ciliary body therefore can he exercised by looking at nearby and distant objects alternatively and repeatedly.

The six extraocular muscles turn or move the eyeball towards a specific direction. Therefore, by looking at objects at various directions alternatively and repeatedly without turning the body or the head, the extraocular muscles are thereby exercised.

The aperture of the pupil is affected by emotion as well as the brightness of the light incident into the eye. The muscle that controls the aperture of the pupil is the circular iris which contains pigment cells and two layers of tissues: one sphincter and one dilator. Under bright light, the sphincter contracts to reduce the aperture while, under no or little light, die dilator contracts to enlarge the aperture. There are also parasympathetic and sympathetic nerves in the iris. Under different emotions, the stimulation to the parasympathetic nerve would cause the aperture to reduce while the stimulation to the sympathetic nerve would cause the aperture to enlarge. Despite that emotion changes indeed could, cause the iris to exercise, this is not a practical approach. More feasible approach would be to subject the eye to significant brightness variations repeatedly.

There are already quite a few methods for exercising various eye muscles. However these methods usually involve repeatedly staring at objects at different distances and directions alternatively, which is rather boring to keep the trainee's patience.

SUMMARY OF THE INVENTION

Accordingly, a novel method for exercising the eye muscles is provided herein. The method provides an exercising environment which contains a display device positioned on a platform, a servo motor to move the platform forward towards a trainee or backward away from the trainee, an illuminating device producing lighting to the exercising environment, a switch to turn on and off tire illuminating device, and a computing device controlling an image displayed on foe display device.

Then, while the trainee is watching the image shown on the display device, by adjusting, the distance of die display device to the trainee, the brightness of the illuminating device, and die location of the image on the display device, all within appropriate ranges and at appropriate frequencies, the ciliary body, the iris, and the extraocular muscles are automatically exercised by the method without boring tire trainee.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Figure 1:
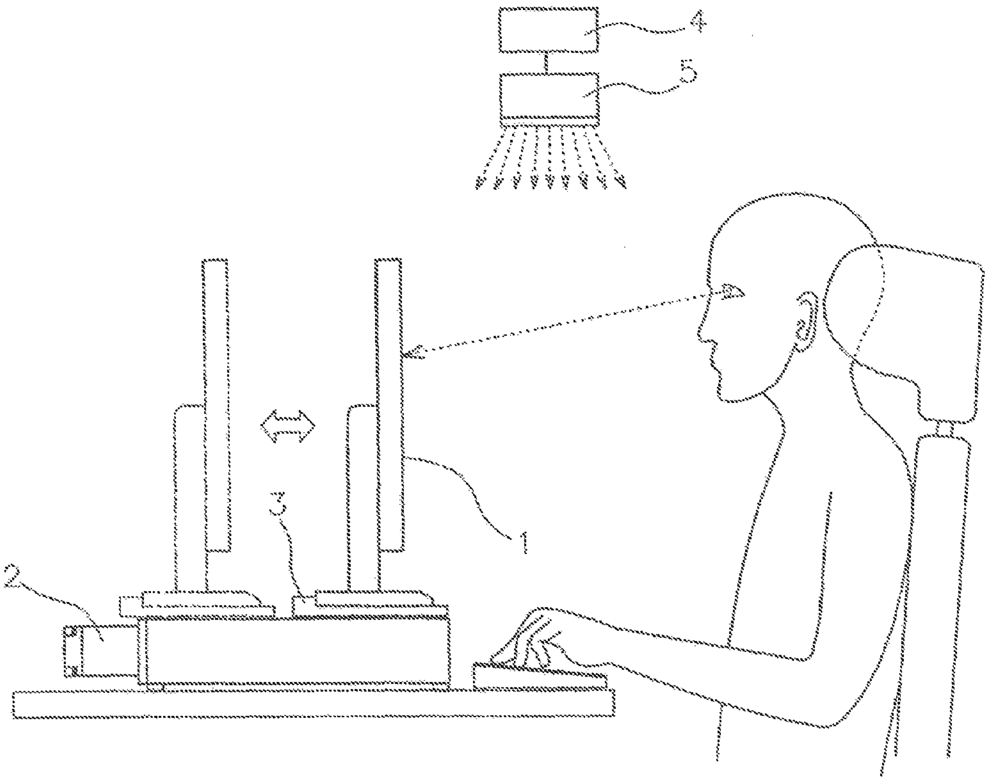
FIG. 1 is a schematic diagram showing an exercising environment provided by an embodiment of the present invention.
Figure 2:
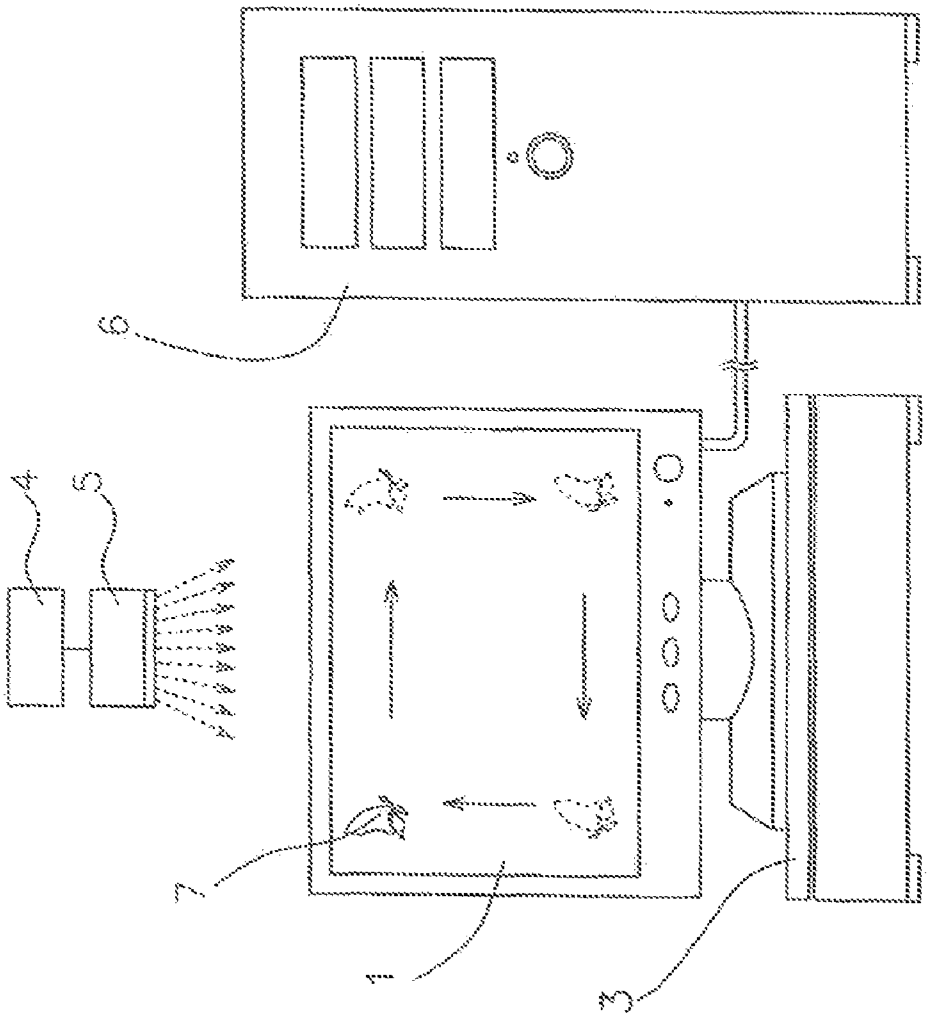
FIG. 2 is another schematic diagram showing die exercising environment of FIG. 1.

An embodiment of the present invention provides an exercising environment for a trainee as shown in FIGS. 1 and 2. As illustrated, a display device 1 such as a LCD screen is positioned on a platform 3 in front of a trainee. The platform 3 is controlled by a servo motor 2, through sliding rails, gears, or mechanical arms to move forward towards the trainee or backward away from the trainee in a linear manner.

In addition, an illuminating device 5 (e.g., a 17 W light bulb) provides lighting to the exercising environment. The illuminating device 5 is controlled by a switch 4 so that the illuminating device 5 is turned on and off at specific intervals. The display device 1 is connected to a computing device 6 which shows a video or an image 7 on the display device 1.

During the exercise, the position and orientation of the trainee's head should be stationary. This can be achieved by providing a head rest or similar supporting device where the trainee's head can be stably rested on.

According to die present invention, the servo motor 2, under the control of a controller, a microprocessor, or the computing device 6, drives the platform 3 so that die distance between the display device 1 and the trainee varies between 5 and 100 cm preferably between 10 and 50 cm. The frequency for foe distance adjustment can be between 1 to 120 times/hr, preferably 5 to 60 times/hr. The distance adjustment according to foe above parameters is conducted while the trainee is watching the video or image 7 shown on foe display device 1 fry the computing device 6. As such, die trainee does not feel bored and, in the mean time, the ciliary body of the trainee is automatically exercised as the display device 1 is moved back and forth.

According to the present invention, the illuminating device 5 is turned on in an ON interval where the illuminating device 5 changes gradually from the dimmest to the brightness, and the illuminating device 5 is turned off in an OFF interval where the illuminating device 5 changes gradually from the brightness to the dimmest. The gradual change in brightness is to avoid over-stimulation to the eye. The switch 4 can be a simple switch or relay driven by a controller, a microprocessor, or the computing device 6 so that there are 1-300 cycles, preferably 3-120 cycles, of ON/OFF intervals per hour. Again, the brightness adjustment according to the above frequency is conducted while the trainee is watching the video or image 7 shown on the display device 1 by she computing device 6. As such, the trainee does not feel bored and, in die mean time, the iris of the trainee is automatically exercised as the illuminating device 5 is turned on and off repeatedly and alternatively. Please note that the distance adjustment of the display device 1 and the brightness adjustment of die illuminating device 5 can be conducted simultaneously or separately.

According to the present invention, die computing device 6 adjusts the location of the video or image 7 shown on the display device 1. For example, the video or image 7 can be shown alternatively at the upper left corner, upper right corner, lower left corner, lower right corner, or any other location. The frequency for die location adjustment can be between 1 and 60 times/hr, preferable between 2 and 15 times/hr. Again, the location adjustment according to the above parameters is conducted while die trainee is watching die video or image 7 shown on the display device 1 by the computing device 6. As such, the trainee does not feel bored and, in the mean time, the extraocular muscles of the trainee are automatically exercised as the video or image 7 is shown at various locations repeatedly and alternatively. Please note that the location adjustment of the displayed video or image 7 can be conducted simultaneously or separately with the brightness adjustment of the illuminating device 5 and/or the distance adjustment of the display device 1.

Please note that the servo motor 2 and die switch 4 can also be connected to and controlled by the computing device 6 and die method of the present invention is implemented as a software program executed by the computing device 6.

It will be understood that each of the elements described above, or two or more together may also find a useful application in other types of methods differing than the type described above.

While certain novel features of this invention have been shown and described and am pointed out in the annexed claim, it is not intended, to be limited to the details above, since it will be understood that various omissions, modifications, substitutions and changes in the forms and details of the device illustrated and in its operation can be made by those skilled in the art without departing in any way from the spirit of the present invention.

I claim:

1. A method for exercising the eye muscles of a trainee comprising the steps of:

providing a display device positioned on a platform in front of said trainee, a servo motor driving said platform to move closer to and former away from said trainee, a switch, an illuminating device connected to and controlled by said switch, and a computing device connected to and showing an image on said display device;

performing at least one of the following tasks:

controlling said servo motor to repeatedly adjust the distance between said display device and said trainee within a distance range at a first frequency:

repeatedly adjusting the location of said image on said display device at a second frequency; and controlling said switch to repeatedly torn on and off said illuminating device at a third frequency.

2. The method according to claim 1, wherein said distance range is between 5 and 100 cm, preferably between 10 and 50 cm.

3. The method according to claim 1, wherein said first frequency is between 1 and 120 times/hr preferably between 5 and 60 times/hr.

4. The method according to claim 1, wherein said second frequency is between 1 and 60 times/hr, preferably between 2 and 15 times/hr.

5. The method according to claim 1, wherein said servo motor is connected to and controlled by said computing device.

6. The method according to claim 1, wherein said switch is connected to and controlled by said computing device.

7. The method according to claim 1, wherein said third frequency is between 1 and 300 times/hr, preferably between 3 and 120 times/hr.

8. The method according to claim 1, wherein said platform is driven by said servo motor via one of a sliding rail, a plurality of gears, and a mechanical arm.

* * * * *